(12) United States Patent
Möller et al.

(10) Patent No.: US 7,317,130 B2
(45) Date of Patent: Jan. 8, 2008

(54) METHOD FOR THE HYDROFORMYLATION OF OLEFINICALLY UNSATURATED COMPOUNDS, ESPECIALLY OLEFINS, IN THE PRESENCE OF CYCLIC CARBONIC ACID ESTERS

(75) Inventors: Oliver Möller, Recklinghausen (DE); Dirk Fridag, Haltern am See (DE); Cornelia Borgmann, Frankfurt (DE); Dieter Hess, Marl (DE); Klaus-Diether Wiese, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 10/525,376

(22) PCT Filed: Aug. 7, 2003

(86) PCT No.: PCT/EP03/08736

§ 371 (c)(1),
(2), (4) Date: May 8, 2006

(87) PCT Pub. No.: WO2004/020380

PCT Pub. Date: Nov. 3, 2004

(65) Prior Publication Data

US 2006/0241324 A1 Oct. 26, 2006

(30) Foreign Application Priority Data

Aug. 31, 2002 (DE) .................. 102 40 253
Jun. 18, 2003 (DE) .................. 103 27 434

(51) Int. Cl.
*C07C 45/50* (2006.01)
(52) U.S. Cl. .................................... 568/451
(58) Field of Classification Search .............. None
See application file for complete search history.

(56) References Cited

U.S. PATENT DOCUMENTS

| | | | |
|---|---|---|---|
| 3,992,453 A * | 11/1976 | Massie ................ 260/604 |
| 4,668,651 A | 5/1987 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,012,008 A * | 4/1991 | Drago et al. ........... 568/454 |
| 5,059,710 A | 10/1991 | Abatjoglou et al. |
| 5,093,534 A | 3/1992 | Ludwig et al. |
| 5,113,022 A | 5/1992 | Abatjoglou et al. |
| 5,138,101 A | 8/1992 | Devon |
| 5,179,055 A | 1/1993 | Wink et al. |
| 5,260,491 A | 11/1993 | Wink et al. |
| 5,264,616 A | 11/1993 | Roeper et al. |
| 5,288,918 A | 2/1994 | Maher et al. |
| 5,360,938 A | 11/1994 | Babin et al. |
| 5,648,554 A | 7/1997 | Mori et al. |
| 5,710,344 A | 1/1998 | Breikss et al. |
| 6,015,928 A | 1/2000 | Gubisch et al. |
| 6,184,424 B1 | 2/2001 | Bueschken et al. |
| 6,187,962 B1 | 2/2001 | Arnoldy et al. |
| 6,239,318 B1 | 5/2001 | Schuler et al. |
| 6,331,657 B1 | 12/2001 | Kaizik et al. |
| 6,403,836 B2 | 6/2002 | Kaizik et al. |
| 6,403,837 B1 | 6/2002 | Hess et al. |
| 6,407,295 B1 | 6/2002 | Kaizik et al. |
| 6,482,992 B2 | 11/2002 | Scholz et al. |
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Röttger et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,009,068 B2 | 3/2006 | Schmutzler et al. |
| 7,109,346 B2 | 9/2006 | Beller et al. |
| 7,193,116 B2 * | 3/2007 | Moeller et al. ............ 568/451 |
| 2003/0144559 A1 | 7/2003 | Hess et al. |
| 2003/0195368 A1 | 10/2003 | Rottger et al. |
| 2004/0236133 A1 | 11/2004 | Selent et al. |
| 2004/0238787 A1 | 12/2004 | Wiese et al. |

(Continued)

FOREIGN PATENT DOCUMENTS

DE     1 953 641     1/1971

(Continued)

OTHER PUBLICATIONS

U.S. Appl. No. 10/584,492, filed Jun. 22, 2006, Ortmann et al.

(Continued)

*Primary Examiner*—Sikarl A. Witherspoon
(74) *Attorney, Agent, or Firm*—Oblon, Spivak, McClelland, Maier & Neustadt, P.C.

(57) ABSTRACT

The present invention relates to a process for preparing aldehydes by hydroformylation of olefinically unsaturated compounds catalyzed by metals of groups 8 to 10 of the Periodic Table of the Elements in the presence of cyclic carbonic esters and ligands which contain no sulfonic acid or sulfonate group.

16 Claims, 3 Drawing Sheets

U.S. PATENT DOCUMENTS

| | | |
|---|---|---|
| 2004/0242947 A1 | 12/2004 | Beller et al. |
| 2005/0043279 A1 | 2/2005 | Selent et al. |
| 2005/0171371 A1 | 8/2005 | Borner et al. |
| 2005/0182277 A1 | 8/2005 | Totsch et al. |
| 2005/0209455 A1 | 9/2005 | Boerner et al. |
| 2005/0234270 A1 | 10/2005 | Kaizik et al. |
| 2005/0256281 A1 | 11/2005 | Grund et al. |
| 2006/0036121 A1 | 2/2006 | Kaizik et al. |
| 2006/0089469 A1 | 4/2006 | Komarov et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0183936 A1 | 8/2006 | Grass et al. |
| 2006/0241324 A1 | 10/2006 | Moeller et al. |

FOREIGN PATENT DOCUMENTS

| | | |
|---|---|---|
| DE | 2 062 703 | 7/1971 |
| DE | 27 15 685 | 10/1977 |
| DE | 28 02 922 | 7/1978 |
| DE | 31 26 265 | 1/1983 |
| DE | 38 42 819 | 6/1990 |
| DE | 44 19 898 | 12/1994 |
| DE | 196 32 600 | 2/1998 |
| DE | 198 10 794 | 9/1999 |
| DE | 199 54 510 | 5/2001 |
| DE | 199 54 721 | 5/2001 |
| EP | 0 017 183 | 10/1980 |
| EP | 0 155 508 | 9/1985 |
| EP | 0 213 639 | 3/1987 |
| EP | 0 214 622 | 3/1987 |
| EP | 0 472 017 | 2/1992 |
| EP | 0 472 071 | 2/1992 |
| EP | 0 518 241 | 12/1992 |
| EP | 0 922 691 | 6/1999 |
| EP | 1 099 677 | 5/2001 |
| EP | 1 099 678 | 5/2001 |
| EP | 1 103 303 | 5/2001 |
| GB | 1 197 902 | 7/1970 |
| GB | 1 312 076 | 4/1973 |
| JP | 07082281 | 3/1995 |
| JP | 09268152 | 10/1997 |
| JP | 10-226662 | 8/1998 |
| JP | 10/279587 | 10/1998 |
| NL | 8700881 | 11/1988 |
| WO | 94/19104 | 9/1994 |
| WO | 95/06627 | 3/1995 |
| WO | 97/08123 | 3/1997 |
| WO | 97/08124 | 3/1997 |
| WO | 97/20795 | 6/1997 |
| WO | 97/40001 | 10/1997 |
| WO | 97/40002 | 10/1997 |
| WO | 98/43935 | 10/1998 |
| WO | 99/38832 | 8/1999 |
| WO | 00/55164 | 9/2000 |
| WO | 01/21627 | 3/2001 |
| WO | 01/68242 | 9/2001 |
| WO | 01/68247 | 9/2001 |
| WO | 01/68248 | 9/2001 |
| WO | 01/68249 | 9/2001 |
| WO | 01/68250 | 9/2001 |
| WO | 01/68251 | 9/2001 |
| WO | 01/68252 | 9/2001 |
| WO | 02/00669 | 1/2002 |
| WO | 02/00670 | 1/2002 |

OTHER PUBLICATIONS

U.S. Appl. No. 10/505,879, filed Sep. 3, 2004, Borgmann.
U.S. Appl. No. 10/525,376, filed May 8, 2006, Moeller et al.
U.S. Appl. No. 10/584,148, filed Jun. 22, 2006, Ortmann et al.
U.S. Appl. No. 10/593,330, filed Sep. 19, 2006, Borgmann et al.
U.S. Appl. No. 10/525,376, filed May 8, 2006, Moeller et al.
U.S. Appl. No. 11/494,741, filed Jul. 28, 2007, Kaizik et al.
U.S. Appl. No. 10/562,454, filed Aug. 18, 2006, Krissmann et al.
U.S. Appl. No. 10/576,302, filed Apr. 19, 2006, Kaizik et al.
U.S. Appl. No. 10/588,762, filed Aug. 8, 2006, Wiese et al.
U.S. Appl. No. 09/708,646, filed Nov. 9, 2000, Hess et al.
U.S. Appl. No. 11/574,063, filed Feb. 22, 2007, Nierlich, et al.

\* cited by examiner

METHOD FOR THE HYDROFORMYLATION OF OLEFINICALLY UNSATURATED COMPOUNDS, ESPECIALLY OLEFINS, IN THE PRESENCE OF CYCLIC CARBONIC ACID ESTERS

BACKGROUND OF THE INVENTION

1. Field of the Invention

The present invention relates to a process for preparing aldehydes by hydroformylation catalyzed by metals of groups 8 to 10 of the Periodic Table of the Elements in the presence of cyclic carbonic esters.

2. Discussion of the Background

The reactions of olefin compounds, carbon monoxide and hydrogen in the presence of a catalyst to form the aldehydes having one more carbon atom are known as hydroformylation (oxo process). Catalysts used in these reactions are frequently compounds of the transition metals of groups 8 to 10 of the Periodic Table of the Elements, in particular compounds of rhodium and of cobalt. In comparison with catalysis by cobalt compounds, hydroformylation using rhodium compounds generally offers the advantage of higher selectivity and is therefore usually more economical. The rhodium-catalyzed hydroformylation is usually carried out using complexes comprising rhodium and preferably trivalent phosphorus compounds as ligands. For example, compounds from the classes of phosphines, phosphites and phosphonites are frequently used as ligands. An overview of the hydroformylation of olefins may be found in B. CORNILS, W. A. HERRMANN, "Applied Homogeneous Catalysis with Organometallic Compounds", Vol. 1&2, VCH, Weinheim, New York, 1996.

Hydroformylations are frequently carried out in the presence of solvents so that the catalyst can easily be recirculated after the reaction product has been separated off. In many continuous hydroformylation processes in which rhodium catalysts are used, the high-boiling mixtures formed as by-product in the hydroformylation are employed as solvents. Such processes are described, for example, in DE 2 062 703, DE 2 715 685, DE 2 802 922 or EP 017183.

In addition to the high boilers, it is possible to use inert organic liquids (DE 3 126 265) and reaction products (aldehydes, alcohols), aliphatic and aromatic hydrocarbons, esters, ethers and water (DE 4 419 898) as solvents. In GB 1 197 902, saturated hydrocarbons, aromatics, alcohols and n-paraffins are used for this purpose.

The addition of one or more polar organic substances in the hydroformylation process is disclosed, for example, in WO 01/68248, WO 01/68249, WO 01/68252. For the present purposes, polar substances are substances from the following classes of compounds: nitriles, cyclic acetals, alcohols, pyrrolidones, lactones, formamides, sulfoxides and water.

The use of carbonic esters as polar additive in cobalt-catalyzed hydroformylation reactions is also known (U.S. Pat. No. 3,992,453). Here, the carbonic ester is not used as solvent but as promoter in the presence of organophosphine complexes. The carbonic esters are used in a molar ratio to the cobalt compound of 1:2. In accordance with the desired catalytic action, the olefin is used in a >100 fold excess over the catalyst metal and the carbonic ester.

The simultaneous use of a polar solvent and a nonpolar solvent has likewise been described in the past (WO 99/38832, WO 01/68247, WO 01/68248, WO 01/68249, WO 01/68250, WO 01/68251, WO 01/68242). The following groups of substances are mentioned as nonpolar solvents: aliphatic, alicyclic and aromatic hydrocarbons, ethers, amines, carboxylic esters, ketones, silanes, silicones and carbon dioxide.

Reasons for the use of polar or nonpolar solvents in hydroformylation reactions are the increased catalyst stability in the reaction and easier work-up of the hydroformylation product. When the catalyst is separated off from the reaction product, e.g. by distillation, deactivation of the catalyst is frequently observed. There have therefore been many attempts to replace the work-up by distillation by a milder process, e.g. by extraction.

Thus, for example, U.S. Pat. No. 6,187,962 and EP 0 922 691 describe a palladium-catalyzed hydroformylation in the presence of sulfones or polynitriles with subsequent separation of the product phase from the catalyst-containing phase and recirculation of the latter. In U.S. Pat. No. 5,648,554, a selective extraction of high boilers and a selection extraction of the catalyst complex using polar solvents such as water, ketones, alcohols, nitriles, amides, diols and carboxylic acids are carried out. U.S. Pat. No. 5,138,101 describes the extraction of the reaction product with alcohol/water mixtures.

In summary, it can be said that a large number of polar and/or nonpolar solvents have been used in hydroformylation reactions.

A person skilled in the art will know that the majority of the solvents mentioned are not at all inert under the conditions of the hydroformylation. For example, aldehydes can react with customary phosphite ligands. The addition of water and/or a carboxylic acid can lead to hydrolytic decomposition of phosphite, phosphonite and phosphinite ligands. Amides can, owing to their complexing properties, displace ligands from the metal center. Alkadienes are known as catalyst poisons. (P. W. N. M. van Leeuven in P. W. N. M. van Leeuven, C. Claver, "Rhodium Catalyzed Hydroformylation", Kluver Academic Publishers, Dordrecht, Boston, London, 2000).

Furthermore, some of the solvents mentioned can reduce the yield by reaction with the aldehydes. Thus, for example, alcohols and diols lead to acetal formation, while the addition of carboxylic acid can catalyze the difficult-to-control aldol reaction.

Furthermore, the known hydroformylation processes are capable of improvement in terms of the selectivity to linear aldehydes, i.e. the use of an additional solvent should in the ideal case not only improve the work-up but also effect an improvement in the selectivity.

JP 10-226662 describes a process for the hydroformylation of olefinic compounds in which a rhodium catalyst is used together with a sodium salt of sulfonated triphenylphosphines as cocatalyst, i.e. a modified catalyst is used. The reaction is carried out in the presence of a polar solvent and a carboxylic acid. As polar solvent, it is possible to use, for example, dimethyl sulfoxide, sulfolane, N-methylpyrrolidone, N,N-dimethylformamide, aceto-nitrile, butanediol, polyalkylene glycols or ethylene carbonate. The polar solvent can be recirculated together with the acid and the catalyst to the hydroformylation reaction. In this process, an alkylene carbonate is used as solvent for the first time. However, a carboxylic acid has to be used in addition to this alkylene carbonate. Although this can be recirculated, the presence of this additional compound can lead to contamination of the desired target product. Firstly, contamination can be by the acid itself, or by-products can be formed by acid catalysis, e.g. by aldolization, and lead to undesirable impurities. The use of the process mentioned is additionally restricted to the hydroformylation of terminal olefins, which are comparatively reactive. In the case of less reactive olefins, viz. internal olefins and especially internal highly branched olefins, the activity of the catalyst is far below that required for industrial use.

It is therefore an object of the present invention to provide a combination of solvent or solvent mixture and ligands for use in a hydroformylation reaction, which does not suffer from the disadvantages described.

SUMMARY OF THE INVENTION

It has now surprisingly been found that in processes in which conventional solvents are used, the yield of the hydroformylation of olefins to the preferred terminal aldehydes can be increased, the work-up of the reaction mixture can be made easier and the catalyst stability can be increased if the catalyzed hydroformylation is carried out in the presence of cyclic carbonic esters as solvents and that the addition of carboxylic acid can be dispensed with if ligands containing no sulfonic acid or sulfonate groups are used.

DETAILED DESCRIPTION OF THE INVENTION

The process of the invention is described below by way of example without the invention being restricted to these particular examples. A person skilled in the art will be able to deduce further variants which are likewise subject matter of the present invention and whose scope is indicated by the description and the claims.

The present invention accordingly provides a process for the hydroformylation of olefinically unsaturated compounds having from 3 to 24 carbon atoms, in particular olefins, in the presence of at least one metal of groups 8-10 of the Periodic Table of the Elements as catalyst, where the hydroformylation is carried out in the presence of at least 0.1 mol %, based on the olefin, of at least one cyclic carbonic ester of the formula I (I)

where $R^1$, $R^2$, $R^3$, $R^4$ are identical or different and are each H or a substituted or unsubstituted aliphatic, alicyclic, aromatic, aliphatic-alicyclic, aliphatic-aromatic or alicyclic-aromatic hydrocarbon radical having from 1 to 27 carbon atoms, n is 0-5 x is a divalent substituted or unsubstituted, aliphatic, alicyclic, aromatic, aliphatic-alicyclic or aliphatic-aromatic hydrocarbon radical having from 1 to 27 carbon atoms, and at least one ligand which contains no sulfonic acid group or sulfonate group.

As a result of the use of ligands which contain no sulfonic acid group or sulfonate group and are, in particular, not sulfonated phosphines, the use of carboxylic acids in the reaction mixture of the hydroformylation can be dispensed with entirely. Preferred ligands are ligands containing nitrogen, phosphorus, arsenic or antimony as donor atoms, and particular preference is given to phosphorus-containing ligands. The ligands can be monodentate or polydentate, and in the case of chiral ligands it is possible to use either the racemate or an enantiomer or diastereomer. As phosphorus ligands, particular mention may be made of phosphines, phosphine oxides, phosphites, phosphonites and phosphinites. Adding no carboxylic acid in the process of the invention makes it possible to use, in combination with carbonates as solvents, ligands which are hydrolyzed in the presence of acid and therefore have a low long-term stability in the presence of acids.

The substituents $R^1$ to $R^4$ and X can be identical or different and be substituted by O, N, NH, N-alkyl or N-dialkyl radicals. Furthermore, these radicals can bear functional groups such as halogens (fluorine, chlorine, bromine, iodine), —OH, —OR, —C(O)alkyl, —CN or —C(O)O-alkyl. Furthermore, C, CH or $CH_2$ groups in these radicals can be replaced by O, N, NH, N-alkyl or N-dialkyl radicals if they are at least three carbon atoms away from the O atom of the ester group. The alkyl groups can once again have from 1 to 27 carbon atoms.

In the process of the invention, preference is given to using ethylene carbonate, propylene carbonate, butylene carbonate or a mixture thereof, for example a mixture (volume ratio=50:50) of ethylene carbonate and propylene carbonate, as cyclic carbonic ester.

It is necessary for the cyclic carbonic esters to be used in an amount of at least 0.1 mol % based on the olefin used or the olefinically unsaturated compound used, preferably an amount within the following ranges:

0.1-$10^6$ mol %
0.1-$10^5$ mol %
0.1-$10^4$ mol %
0.1-$10^3$ mol %
0.1-100 mol %
0.1-10 mol %
0.1-1 mol %.

It is possible to use further solvents in addition to the cyclic carbonic esters. In particular process variants, the hydroformylation reaction of the invention is therefore carried out in the presence of at least 0.1 mol %, based on the olefin or the olefinically unsaturated compound, of at least one solvent which is immiscible with the cyclic carbonic ester I.

Carbonic esters of the formula I have a dielectric constant of over 30.

The nonpolar solvents which are immiscible with the cyclic carbonic esters and are used in the process of the invention have dielectric constants of less than 20, preferably from 1.1 to 10, particularly preferably from 1.1 to 5.

Possible nonpolar solvents are substituted or unsubstituted hydrocarbons having from 5 to 50 carbon atoms, e.g. the high-boiling by-products of the hydroformylation reaction, Texanol or the isomer mixtures obtained in the tetramerization or pentamerization of propene or butene with subsequent hydrogenation, i.e. tetrabutane, pentabutane, tetrapropane and/or pentapropane. It is likewise possible to use olefins or olefinically unsaturated compounds having 3-24 carbon atoms, in particular the olefin or the olefinically unsaturated compound used for the hydroformylation, as starting material.

To avoid by-products, the nonpolar solvents should be largely inert under the conditions of the hydroformylation reaction.

In the process of the invention, the reaction mixture can be present as a single phase or as two phases in the hydroformylation reactor over the entire conversion range. However, it is also possible for the feed mixture to be initially made up of two phases at a low conversion and to become a single phase at higher conversions during the course of the reaction.

It is possible for a single-phase feed mixture to become a two-phase product mixture during the process of the invention.

The process of the invention can be carried out using various catalytically active metals and, if desired, various ligands.

Possible catalytically active metals are the metals of groups 8 to 10 of the Periodic Table of the Elements, for example rhodium, cobalt, platinum or ruthenium.

The process of the invention is, as mentioned above, carried out in the presence of ligands such as phosphonites, phosphites, phosphine oxides, phosphines and/or phosphinites or phosphinines or phosphinanes.

The choice of the added ligands for the metal in the process of the invention is restricted only in that no ligands containing sulfonic acid groups or sulfonate groups are used, in particular no sulfonated arylphosphines. The choice of ligands added depends, in particular, on the olefin or olefin mixture used or on the olefinically unsaturated compounds used and on the desired products. Preferred ligands are ligands which contain nitrogen, phosphorus, arsenic or antimony as donor atoms; particular preference is given to phosphorus-containing ligands. The ligands can be monodentate or polydentate, and in the case of chiral ligands, either the racemate or one enantiomer or diastereomer can be used. Particularly important examples of phosphorus ligands are phosphines, phosphine oxides, phosphites, phosphonites and phosphinites.

Examples of phosphines are triphenylphosphine, tris(p-tolyl)phosphine, tris(m-tolyl)phosphine, tris(o-tolyl)phosphine, tris(p-methoxyphenyl)phosphine, tris(p-fluorophenyl)phosphine, tris(p-chlorophenyl)phosphine, tris(p-dimethylaminophenyl)phosphine, ethyldiphenylphosphine, propyldiphenylphosphine, t-butyldiphenylphosphine, n-butyldiphenylphosphine, n-hexyldiphenylphosphine, c-hexyldiphenylphosphine, dicyclohexylphenylphosphine, tricyclohexylphosphine, tricyclopentylphosphine, triethylphosphine, tri(1-naphthyl)phosphine, tri-2-furylphosphine, tribenzylphosphine, benzyldiphenylphosphine, tri-n-butylphosphine, tri-i-butylphosphine, tri-t-butylphosphine, bis(2-methoxyphenyl)phenylphosphine, neomenthyldiphenylphosphine, 1,2-bis(dicyclohexylphosphino)ethane, bis(dicyclohexylphosphino)methane, 1,2-bis(diethylphosphino)ethane, 1,2-bis(2,5-diethylphospholano)benzene [Et-DUPHOS], 1,2-bis(2,5-diethylphospholano)ethane [Et-BPE], 1,2-bis(dimethylphosphino)ethane, bis(dimethylphosphino)methane, 1,2-bis(2,5-dimethylphospholano)benzene [Me-DUPHOS], 1,2-bis(2,5-dimethylphospholano)ethane [Me-BPE], 1,2-bis(diphenylphosphino)benzene, 2,3-bis(diphenylphosphino)bicyclo[2.2.1]hept-5-ene [NORPHOS], 2,2'-bis(diphenylphosphino)-1,1'-binaphthyl [BINAP], 2,2'-bis(diphenylphosphino)-1,1'-biphenyl [BISBI], 2,3-bis(diphenylphosphino)butane, 1,4-bis(diphenylphosphino)butane, 1,2-bis(diphenylphosphino)ethane, bis(2-diphenylphosphinoethyl)phenylphosphine, 1,1'-bis(diphenylphosphino)ferrocene, bis(diphenylphosphino)methane, 1,2-bis(diphenylphosphino)propane, 2,2'-bis(di-p-tolylphosphino)-1,1'-binaphthyl, O-isopropylidene-2,3-dihydroxy-1,4-bis(diphenylphosphino)butane [DIOP], 2-(diphenylphosphino)-2'-methoxy-1,1'-binaphthyl, 1-(2-diphenylphosphino-1-naphthyl)isoquinoline, 1,1,1-tris(diphenylphosphino)ethane, and/or tris(hydroxypropyl)phosphine.

Examples of phosphinines include 2,6-dimethyl-4-phenylphosphinine, 2,6-bis(2,4-dimethylphenyl)-4-phenylphosphinine and also further ligands described in WO 00/55164. Examples of phosphinanes include 2,6-bis(2,4-dimethylphenyl)-1-octyl-4-phenylphosphinane, 1-octyl-2,4,6-triphenylphosphinane and further ligands described in WO 02/00669.

Examples of phosphites are trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl)phosphite, triphenyl phosphite, tris(2,4-di-t-butylphenyl)phosphite, tris(2-t-butyl-4-methoxyphenyl)phosphite, tris(2-t-butyl-4-methylphenyl)phosphite, tris(p-cresyl)phosphite. Further examples are sterically hindered phosphite ligands as are described, inter alia, in EP 155 508, U.S. Pat. No. 4,668,651, U.S. Pat. No. 4,748,261, U.S. Pat. No. 4,769,498, U.S. Pat. No. 4,774,361, U.S. Pat. No. 4,835,299, U.S. Pat. No. 4,885,401, U.S. Pat. No. 5,059,710, U.S. Pat. No. 5,113,022, U.S. Pat. No. 5,179,055, U.S. Pat. No. 5,260,491, U.S. Pat. No. 5,264,616, U.S. Pat. No. 5,288,918, U.S. Pat. No. 5,360,938, EP 472 071, EP 518 241 and WO 97/20795. Triphenyl phosphites which are substituted by 1 or 2 isopropyl and/or tert-butyl groups on the phenyl rings, preferably in the ortho position relative to the phosphite ester group, are preferably used. Bisphosphite ligands which are described, inter alia, in EP 1 099 677, EP 1 099 678, WO 02.00670, JP 10279587, EP 472017, WO 01/21627, WO 97/40001, WO 97/40002, U.S. Pat. No. 4,769,498, EP 213639 and EP 214622 are particularly preferably used.

Examples of phosphonites are methyldiethoxyphosphine, phenyldimethoxyphosphine, phenyldiphenoxyphosphine, 6-phenoxy-6H-dibenz[c,e] [1,2]oxaphosphorin and their derivatives in which all or some of the hydrogen atoms are replaced by alkyl or aryl radicals or halogen atoms and ligands as described in WO 98/43935, JP 09-268152 and DE 198 10 794 and in the German patent applications DE 199 54 721 and DE 199 54 510.

Customary phosphinite ligands are described, inter alia, in U.S. Pat. No. 5,710,344, WO 95 06627, U.S. Pat. No. 5,360,938, JP 07082281. Examples are diphenyl(phenoxy)phosphine and its derivatives in which all or some of the hydrogen atoms are replaced by alkyl or aryl radicals or halogen atoms, diphenyl(methoxy)phosphine, diphenyl(ethoxy)phosphine, etc.

The active catalyst complex for the hydroformylation reaction is formed from a salt or a compound of the metal (catalyst precursor), the ligand and synthesis gas. This advantageously occurs in situ during the hydroformylation. Customary catalyst precursors are, for example, octanoates, nonanoates or acetylacetonates. The molar ratio of metal to ligand is from 1/1 to 1/1000, preferably from 1/1 to 1/50. The concentration of the metal in the reaction mixture is preferably in the range from 1 ppm to 1000 ppm, preferably in the range from 5 ppm to 300 ppm.

The starting materials for a hydroformylation by the process of the invention are compounds which contain ethylenically (olefinically) unsaturated C—C double bonds, olefins or mixtures of olefins, especially monoolefins having from 3 to 24, preferably from 4 to 16, particularly preferably from 3 to 12, carbon atoms, having terminal or internal C—C double bonds, e.g. 1- or 2-pentene, 2-methyl-1-butene, 2-methyl-2-butene, 3-methyl-1-butene, 1-, 2- or 3-hexene, the $C_6$-olefin mixture obtained in the dimerization of propene(dipropene), heptenes, 2- or 3-methyl-1-hexene, octenes, 2-methylheptenes, 3-methylheptenes, 5-methyl-2-heptene, 6-methyl-2-heptene, 2-ethyl-1-hexene, the isomeric $C_8$-olefin mixture obtained in the dimerization of butenes(dibutene), nonenes, 2- or 3-methyloctenes, the $C_9$-olefin mixture obtained in the trimerization of propene (tripropene), decenes, 2-ethyl-1-octene, dodecenes, the $C_{12}$-olefin mixture obtained in the tetramerization of propene or the trimerization of butenes(tetrapropene or tributene), tetradecenes, hexadecenes, the $C_{16}$-olefin mixture obtained in the tetramerization of butenes(tetrabutene) and olefin mixtures prepared by cooligomerization of olefins having different numbers of carbon atoms (preferably from 2 to 4), if appropriate after separation into fractions having an identical or similar chain length by distillation. It is likewise possible to use olefins or olefin mixtures which have been obtained by the Fischer-Tropsch synthesis and olefins which have been obtained by oligomerization of ethene or olefins which are obtainable via metathesis reactions. Preferred starting materials are $C_4$-, $C_8$-, $C_9$-, $C_{12}$- or $C_{16}$-olefin mixtures.

The volume ratio of carbon monoxide to hydrogen in the synthesis gas is generally in the range from 2:1 to 1:2, in particular 1:1. The synthesis gas is advantageously used in excess, for example in an amount up to three times the stoichiometric amount.

The hydroformylations are generally carried out at pressures of from 1 to 350 bar, preferably at pressures of from 15 to 270 bar. The pressure employed depends on the structure of the feed olefins, the catalyst used and the desired effect. Thus, for example, α-olefins can be converted into the corresponding aldehydes in high space-time yields in the presence of rhodium catalysts at pressures of less than 64 bar. In contrast, in the case of olefins having internal double bonds, in particular branched olefins, higher pressures are advantageous.

The reaction temperatures in the process of the invention are from 20 to 250° C., preferably from 60° C. to 180° C., more preferably from 90° C. to 150° C.

After the hydroformylation, the major part of the synthesis gas can be removed by depressurization.

After the hydroformylation reaction, the separation of product and catalyst solution is preferably carried out by means of phase separation with the aid of thermal separation processes.

The reactor output comprising any unreacted olefins or olefinically unsaturated compounds, reaction products, reaction by-products, at least one cyclic carbonic ester, possibly a nonpolar solvent, the catalyst and possibly free ligand is introduced into a phase separation apparatus, e.g. a residence vessel (settler), which can optionally be preceded by a heat exchanger for cooling the reactor output. According to the present invention, the phase separation is carried out at temperatures of from 0° C. to 130° C., preferably from 10° C. to 60° C. The phase separation is carried out at pressures of from 1 bar to 270 bar, but preferably at the same pressure as that selected in the hydroformylation step.

Depending on the starting materials used, the separation in the phase separation vessel results in, for example, a relatively light phase which consists essentially of unreacted olefins or olefinically unsaturated compounds, catalyst complex and optionally free ligand and a nonpolar solvent and is returned to the reactor and a heavier phase which comprises predominantly at least one cyclic carbonic ester, reaction products and reaction by-products and is worked up further. According to the invention, this is achieved by separation into aldehydes (alcohols), unreacted olefins or olefinically unsaturated compounds, residual solvents and by-products and can be carried out, for example, by distillation. Solvent which has been separated off is recirculated to the hydroformylation reactor.

The composition of these phases is determined by the type of ligands used, residual olefin or aldehyde content and the type and amount of, solvents used. For this reason, a different composition of the phases can easily be observed.

The process of the invention can be carried out in a number of variants.

Variant A

In this process variant, the output from the hydroformylation reaction is separated into a fraction comprising predominantly the catalyst and the cyclic carbonic ester and a fraction comprising predominantly the hydroformylation products.

This process variant can be employed when a polar catalyst and an optional further nonpolar solvent are used. The nonpolar solvent can also be identical to the feed olefin or the olefinically unsaturated compound(s) used, so that either the hydroformylation reaction is not carried out to full conversion (e.g. only to 90%, preferably 80%) or the olefin or the olefinically unsaturated compound is added during or after the hydroformylation reaction.

Figure 1:
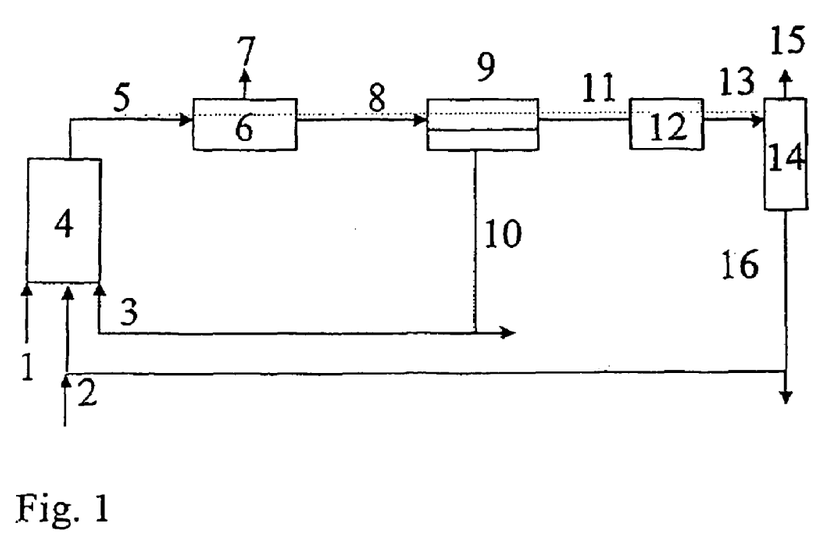
FIGS. 1-3 each illustrate a variant of the process of the present invention, respectively.

Variant A of the process is illustrated by FIG. 1 synthesis gas (1), olefins or olefinically unsaturated compounds (2) and catalyst solution (3), which advantageously comprises the cyclic carbonic esters, are reacted in the hydroformylation reactor (4). The reactor output (5) can optionally be freed of excess synthesis gas (7) in a depressurization vessel (6). The stream (8) obtained in this way is preferably separated in a settler (9) into a heavy phase (10) which comprises the major part of the cyclic carbonic ester and the catalyst and a light phase (11) which comprises the hydroformylation products, unreacted olefin or olefinically unsaturated compound and, if applicable, the nonpolar solvent. Depending on the catalyst system used, it can be advantageous to remove catalyst residues from the further process by means of an appropriate separation stage (12). Stream (11) or (13) is then passed to the separation stage (14). Here, the reaction products (alcohol and aldehyde) (15) are separated off and passed to further work-up or hydrogenation. The fraction (16) which has likewise been separated off comprises, for example, residual cyclic carbonic ester, high-boiling by-products, reaction products and, if applicable, the further nonpolar solvent which has been added. Fraction (16) can be recirculated to the hydroformylation reactor (4). This is advantageously preceded by a work-up in which undesirable by-products are discharged and discarded. The catalyst separation can also be carried out as an extraction by feeding at least part of the fraction (16) directly into the stream (8). The extraction can be a single-stage extraction or be operated as a multistage process in countercurrent, cocurrent or cross-current.

Variant B

In this process variant, the reactor output from the hydroformylation reaction is separated into a fraction comprising predominantly the catalyst and a nonpolar solvent and a fraction comprising predominantly the hydroformylation products and the cyclic carbonic ester.

Figure 2:
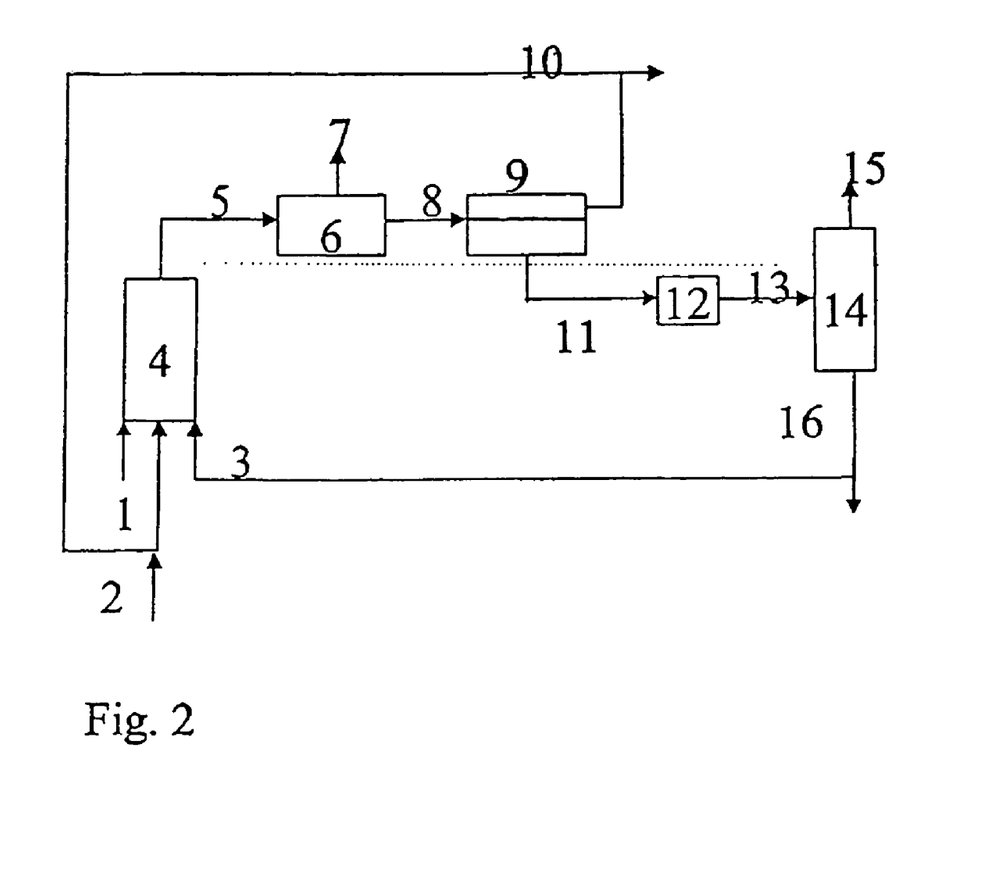

Variant B is preferably employed when a nonpolar solvent or solvent mixture which is immiscible with the cyclic carbonic ester is added. This variant can be employed especially when either no further feed olefin or no further olefinically unsaturated compound is to be added or when the hydroformylation reaction is carried out to a high or complete conversion. Addition of a nonpolar solvent makes the variant B particularly useful when using nonpolar catalyst systems comprising, for example, phosphite ligands. The process variant B is illustrated below by FIG. 2: In the hydroformylation reactor (4), synthesis gas (1) and olefin or olefinically unsaturated compound(s) (2) which advantageously contains/contain the nonpolar solvent and the catalyst are reacted in the presence of the cyclic carbonic esters (3). The reactor output (5) is optionally freed of excess synthesis gas (7) in a separation vessel (6) and passed as stream (8) to the separation vessel (9). Here, a light phase (10) comprising the catalyst, unreacted olefin or unreacted olefinically unsaturated compound and the nonpolar solvent is separated from a heavy phase (11) comprising the reaction products and the cyclic carbonic esters. The fraction (10) is advantageously recirculated to the hydroformylation reactor. Fraction (11) can optionally be freed of catalyst residues in a vessel (12) and is then passed to the distillation stage (14). Here, the reaction products (15) are separated from the cyclic carbonic esters (16) which are recirculated to the hydroformylation rector (4). The catalyst separation can also be carried out as an extraction by introducing at least part of the fraction (16) into the stream (8). The extraction can be a single-stage extraction or be operated as a multistage process in countercurrent, cocurrent or cross-current.

Variant C

In this hydroformylation reaction, separation is carried out into a fraction comprising predominantly the catalyst and olefin or olefinically unsaturated compounds and a fraction comprising predominantly the hydroformylation products and the cyclic carbonic ester.

Various olefins or olefinically unsaturated compounds, olefin mixtures or isomer mixtures can be added before and after the hydroformylation reaction. Preference is given to using the same olefins/olefin mixtures or olefinically unsaturated compounds.

This process variant is particularly useful when a nonpolar catalyst is used and when no additional nonpolar solvent is to be employed. Within process variant C, further variants are possible: additional olefin or olefinically unsaturated compound can be fed in after the actual hydroformylation reaction or the hydroformylation reaction is carried out only to a particular partial conversion (for example 50-70%).

Figure 3:
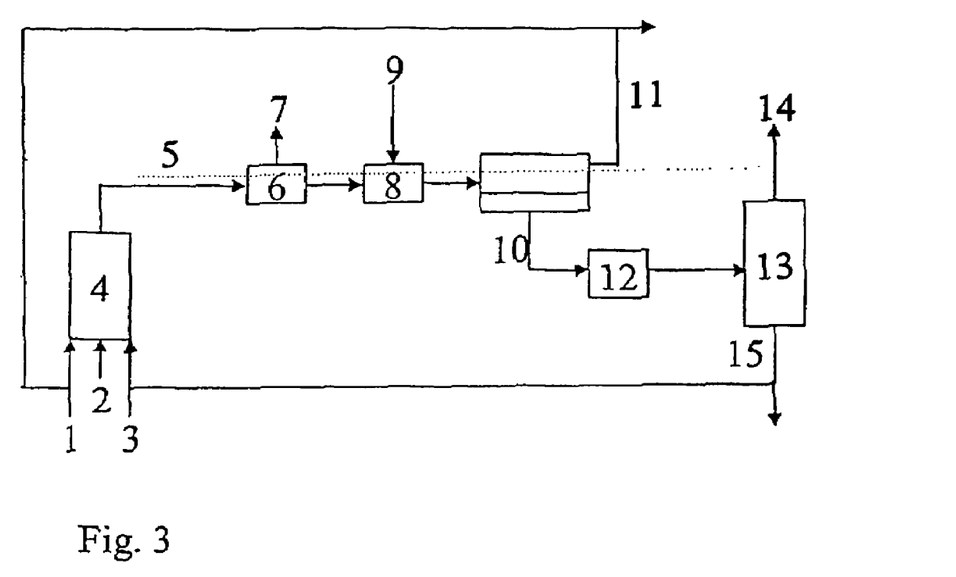

FIG. 3 illustrates this process variant: in the hydroformylation reactor (4), olefin or olefinically unsaturated compound (1) and synthesis gas (2) are reacted in the presence of cyclic carbonic esters (3). The catalyst is advantageously present in the olefin phase. The output from the hydroformylation reactor (5) can be freed of excess synthesis gas (7) in a vessel (6) and is subjected to a phase separation in a suitable vessel. Before this, fresh feed olefin (9) can be introduced via a mixing section (8). When olefinic compounds are introduced, cooling of the reactor output by means of a heat exchanger (not shown) is generally necessary. The phase separation produces a light phase (11) which comprises the olefin or the olefinically unsaturated compound and the catalyst; this phase is recirculated to the hydroformylation reactor (4). The heavy phase (10) comprises the reaction products and the cyclic carbonic ester and is, after an optional catalyst removal (12), subjected to a distillation (13). Here, the reaction products (14) are separated off from the cyclic carbonic ester (15) which is recirculated to the hydroformylation reactor. The catalyst separation can also be carried out as a single-stage extraction or as a multistage, countercurrent, cocurrent or cross-current extraction.

The abovementioned variants of the process of the invention include the separation of the reactor output and optionally the hydroformylation products; this can be carried out, for example, by distillation. However, the use of other separation processes, e.g. extraction as described, inter alia, in WO 01/68247, EP 0 922 691, WO 99/38832, U.S. Pat. No. 5,648,554 and U.S. Pat. No. 5,138,101 or permeation as described, inter alia, in DE 195 36 41, GB 1312076, NL 8700881, DE 38 42 819, WO 94/19104, DE 196 32 600 and EP 1 103 303, is also possible. When the separation is carried out industrially, various methods can be employed. The separation is preferably carried out by means of falling film evaporators, short-path evaporators or thin film evaporators or combinations of these apparatuses. The advantage of such a combination can be, for example, that synthesis gas still dissolved in the mixture and part of the products and of the starting olefins still present can be separated off in a first step (for example in a falling film evaporator) and the catalyst can finally be separated off in a second step (for example in a thin film evaporator).

The extractive separation is advantageously carried out continuously. It can be configured as a single-stage process or be operated as a multistage process in countercurrent or cross-current.

The reaction product mixtures which have been freed of catalyst, excess synthesis gas and the major part of the solvent (cyclic carbonic ester) are then separated into aldehydes (alcohols), olefins or olefinically unsaturated compounds, solvents and by-products. This can be achieved, for example, by distillation. Olefin or olefinically unsaturated compound and/or solvent which have/has been separated off from the reaction product mixture or the hydroformylation products can be recirculated to the hydroformylation reaction.

When the target products are not the aldehydes themselves but instead the alcohols derived from them, the reaction product mixture which has been freed of synthesis gas and catalyst and possibly of solvent can be hydrogenated before or after olefin has been separated off (the olefinically unsaturated compound has been separated off) and subsequently be worked up by distillation to give pure alcohol.

In all process variants, the fraction comprising the catalyst is advantageously recirculated to the hydroformylation reaction. This is of course independent of the composition of the fractions in which the catalyst is dissolved.

The process of the invention can be carried out in one or more stages. Here, it is possible for a first hydroformylation reaction to be followed by a second hydroformylation stage which converts the internal olefins, which are difficult to hydroformylate, into the desired aldehydes under "more severe" operating conditions. However, preference is given to a separation of unreacted olefins and products being carried out first and the unreacted products being passed to a further hydroformylation stage. Here, a distinction is once again to be made between the various process variants; in the case of those process variants in which unreacted olefins, catalyst and possibly also free ligand are present in various fractions after the separation of the reactor output, it is possible to use a completely different catalyst system (different metal and/or different ligands) in the second hydroformylation stage. If unreacted olefins, catalyst and possibly free ligand are not present in various fractions, this is of course not possible. In this case, it can be advantageous to add a higher concentration of catalysts or ligand systems to the unreacted olefins in order to convert olefins which are more difficult to hydroformylate into the desired products. In all cases, it is necessary to add the abovementioned amounts of the cyclic carbonic esters in the further hydroformylation stages.

The use of cyclic carbonic esters is also conceivable for other metal-catalyzed reactions. Application areas are, for example, cyanation, hydrocyanation, isomerization of olefins, hydrations, Heck reactions, condensation reactions such as the aldol condensation or hydration or esterification reactions.

The following examples are merely for the purposes of illustrating the invention and do not restrict its scope which is defined by the description and the claims.

EXAMPLE 1

Variant A

A 3 l stirring autoclave was charged under nitrogen with 1070 g of propylene carbonate, 0.22 g of rhodium nonanoate and 3.4 g of tris(2,4-di-tert-butylphenyl)phosphite. The rhodium concentration in the reaction mixture was 40 ppm and the molar ratio of phosphorus to rhodium was 10. After heating to 100° C. under synthesis gas (molar ratio of hydrogen to carbon monoxide=1:1), 280 g of 1-octene were introduced. Hydroformylation was carried out at a reaction pressure of 20 bar and a temperature of 100° C. while stirring.

After a reaction time of 50 minutes, the conversion of 1-octene was 76%. The selectivity to n-nonanal was 65%. This corresponded to an n-nonanal yield of 49.4%.

EXAMPLE 2

Comparative Experiment for Example 1

A further experiment was carried out in a manner analogous to Example 1 with the difference that tetrabutane was used as solvent in place of propylene carbonate.

After hydroformylation for 50 minutes, the conversion of 1-octene was 92% and the selectivity to n-nonanal was 34%.

This corresponds to an n-nonanal yield of 31.3%.

Comparison of these two experiments shows that the selectivity to and yield of linear aldehydes can be increased by use of propylene carbonate.

EXAMPLE 3

Variant B 1070 g of propylene carbonate, 0.26 g of rhodium nonanoate, 5.7 g of a bidentate phosphite ligand of the formula II and 273 g of n-decane were placed under nitrogen in a 3 l autoclave. This corresponds to a rhodium concentration of 40 ppm and a molar ratio of phosphorus to rhodium of 20. After heating to 100° C. under synthesis gas pressure (molar ratio of CO—H$_2$=1:1), 280 g of a mixture of internal octenes were introduced.

The hydroformylation was carried out at a temperature of 100° C. and a synthesis gas pressure of 20 bar. After the reaction was complete, the mixture was cooled to ambient temperature and a phase separation was carried out. The hydrocarbon phase containing the active catalyst complex remained in the reactor. The propylene carbonate phase which contained most of the aldehyde was drained from the reactor and worked up in a thin film evaporator at 125° C. and 25 hPa to give the crude aldehyde. The propylene carbonate obtained as bottom product was reused together with 140 g of olefin mixture and the catalyst solution remaining in the reactor in another hydroformylation using the above procedure. (The reuse is carried out a total of eight times, cf. Table 1, experiments 3.1 to 3.8.)

(II)

EXAMPLE 4

Comparative Experiment for Example 3

A further series of experiments was carried out using a method analogous to Example 3 but with the following differences: tetrabutane was used as solvent in place of propylene carbonate and n-decane (this tetrabutane is a mixture of C$_{16}$-alkanes formed by oligomerization and subsequent hydrogenation of 1-butene).

After the reaction was complete, the total reaction mixture was distilled in a thin film evaporator at 125° C. and 25 hPa. This gave the crude aldehyde as top product. The bottom product was a hydrocarbon mixture comprising predominantly tetrabutane together with the catalyst. This solution was reused together with 140 g of olefin mixture in another hydroformylation using the above procedure. (The reuse is carried out a total of eight times, cf. Table 1, experiments 4.1 to 4.8.)

In the series of experiments described in Examples 3 and 4, the conversion was determined by on-line measurement of the consumption of synthesis gas. The time-dependence of the conversion makes it possible to calculate an overall rate constant which is a measure of the catalyst activity. Various reaction systems can be compared with the first reaction of a series of experiments by normalization to the overall rate constant.

Table 1 summarizes the normalized overall rate constants for a number of reuse cycles from the examples.

The comparison shows that the catalyst activity remains readily constant in the example according to the invention, while a significant decrease in the catalyst activity is observed in the case of the conventional procedure employed in the comparative example. The catalyst stability can thus be increased considerably by use of the process of the invention.

TABLE 1

Comparison of Examples 3 and 4

| Example 3 | Rel. Overall rate const. [−] | Example 4 | Rel. Overall rate const. [−] |
|---|---|---|---|
| 3.0 | 1 | 4.0 | 1.000 |
| 3.1 | 1.110 | 4.1 | 0.855 |
| 3.2 | 1.035 | 4.2 | 0.909 |
| 3.3 | 0.982 | 4.3 | 0.726 |
| 3.4 | 0.990 | 4.4 | 0.834 |
| 3.5 | 0.942 | 4.5 | 0.728 |
| 3.6 | 1.009 | 4.6 | — |
| 3.7 | 0.805 | 4.7 | 0.592 |
| 3.8 | 1.000 | 4.8 | 0.313 |

Note:
In the case of Example 4.6, the measurement was defective, so that no value can be reported.

The invention claimed is:

1. A process comprising hydroformylating an olefinically unsaturated compound having from 3 to 24 carbon atoms in the presence of at least one metal of groups 8 to 10 of the Periodic Table of the Elements as catalyst, wherein the hydroformylation is carried out in the presence of at least 0.1 mol %, based on the olefinically unsaturated compound, of at least one cyclic carbonic ester of the formula I (I)

where
$R^1$, $R^2$, $R^3$, $R^4$ are identical or different and are each H or a substituted or unsubstituted aliphatic, alicyclic, aromatic, aliphatic-alicyclic, aliphatic-aromatic or alicyclic-aromatic hydrocarbon radical having from 1 to 27 carbon atoms,
n is 0-5
X is a divalent substituted or unsubstituted, aliphatic, alicyclic, aromatic, aliphatic-alicyclic or aliphatic-aromatic hydrocarbon radical having from 1 to 27 carbon atoms,
and at least one ligand which contains no sulfonic acid group or sulfonate group, wherein the cyclic carbonic ester component is present in solvent amounts for the catalyst.

2. The process as claimed in claim 1, wherein $R^1$, $R^2$, $R^3$, $R^4$ and X are substituted by identical or different substituents selected from among O, N, NH, N-alkyl and N-dialkyl radicals, fluorine, chlorine, bromine, iodine, —OH, OR, —CN, —C(O)alkyl or —C(O)O-alkyl.

3. The process as claimed in claim 1, wherein the hydroformylation is carried out in the presence of at least 0.1 mol %, based on the olefinically unsaturated compound, of at least one solvent which is relatively nonpolar compared to the cyclic carbonic ester I and is immiscible with the cyclic carbonic ester I.

4. The process as claimed in claim 3, wherein substituted or unsubstituted hydrocarbons having from 5 to 50 carbon atoms, olefinically unsaturated compounds or olefins having from 3 to 24 carbon atoms are used as nonpolar solvent.

5. The process as claimed in claim 1, wherein the output from the hydroformylation reaction is separated into a fraction comprising predominantly the catalyst and the cyclic carbonic ester and a fraction comprising predominantly the hydroformylation products.

6. The process as claimed in claim 3, wherein the output from the hydroformylation reaction is separated into a fraction comprising predominantly the catalyst and a nonpolar solvent and a fraction comprising predominantly the hydroformylation products and the cyclic carbonic ester.

7. The process as claimed in claim 1, wherein the output from the hydroformylation reaction is separated into a fraction comprising predominantly the catalyst and unreacted olefinically unsaturated compounds and a fraction comprising predominantly the hydroformylation products and the cyclic carbonic ester.

8. The process as claimed in claim 1, wherein the fraction comprising the catalyst is recirculated to the hydroformylation reaction.

9. The process as claimed in claim 1, wherein the cyclic carbonic ester used is ethylene carbonate, propylene carbonate or butylene carbonate or a mixture thereof.

10. The process as claimed in claim 1, wherein the hydroformylation is carried out in the presence of phosphonites, phosphites, phosphine oxides, phosphines, phosphinites, phosphinines and/or phosphinanes.

11. The process as claimed in claim 1, wherein unreacted olefinically unsaturated compounds (olefins) are separated off from the reactor output or from the hydroformylation products and are recirculated to the hydroformylation reaction.

12. The process as claimed in claim 1, wherein unreacted olefinically unsaturated compounds are separated off from the reactor output or from the hydroformylation products and are used in a second reaction stage.

13. The process as claimed in claim 1, which is carried out in the absence of carboxylic acids.

14. The process as claimed in claim 1, wherein the metal comprises rhodium.

15. The process as claimed in claim 9, wherein the cyclic carbonic ester used comprises propylene carbonate.

16. The process as claimed in claim 1, wherein the cyclic carbonic ester component is present in an amount by weight greater than the amount of olefinically unsaturated compound.

* * * * *